United States Patent [19]

Vosika et al.

[11] Patent Number: 4,950,645
[45] Date of Patent: Aug. 21, 1990

[54] COMPOSITION FOR MACROPHAGE ACTIVATION

[75] Inventors: Gerald J. Vosika; Dennis A. Cornelius, both of Fargo, N. Dak.; Karl E. Swenson, Gahanna, Ohio

[73] Assignee: ImmunoTherapeutics, Inc., Fargo, N. Dak.

[21] Appl. No.: 216,789

[22] Filed: Jul. 8, 1988

[51] Int. Cl.⁵ .................. A61K 37/02; C07K 9/00
[52] U.S. Cl. ............................ 514/8; 424/88; 530/322
[58] Field of Search ............... 514/8; 530/322; 424/88-92

[56] References Cited

U.S. PATENT DOCUMENTS

| | | |
|---|---|---|
| 3,976,544 | 8/1976 | Adam et al. .................. 195/2 |
| 4,042,678 | 8/1977 | Ciorbaru et al. .............. 424/12 |
| 4,094,971 | 6/1978 | Chedid et al. ................ 424/92 |
| 4,101,536 | 7/1978 | Yamamura et al. ........ 260/112.5 R |
| 4,153,684 | 5/1979 | Audibert et al. .............. 24/88 |
| 4,158,052 | 6/1979 | Audibert et al. .............. 424/45 |
| 4,172,125 | 10/1979 | Audibert et al. ............. 424/89 |
| 4,185,089 | 1/1980 | Derrien et al. ............... 424/88 |
| 4,186,194 | 1/1980 | Adams et al. ................ 424/89 |
| 4,235,771 | 11/1980 | Adam et al. .............. 260/112.5 R |
| 4,256,735 | 3/1981 | Durett ....................... 424/88 |
| 4,271,151 | 6/1981 | Hotta ......................... 514/18 |
| 4,272,524 | 6/1981 | Chedid et al. ............... 424/177 |
| 4,317,771 | 3/1982 | Shiba et al. ............... 260/112.5 R |
| 4,323,559 | 4/1982 | Audibert et al. ............. 424/177 |
| 4,357,322 | 11/1982 | Rooks, II et al. ........... 424/177 |
| 4,357,323 | 11/1982 | Soma ......................... 536/1 |
| 4,370,265 | 1/1983 | Adams et al. ............... 424/177 |
| 4,382,080 | 5/1983 | Shiba et al. ................ 424/177 |
| 4,391,800 | 7/1983 | Durette et al. .............. 424/177 |
| 4,395,399 | 7/1983 | Ovchinnikov et al. ........ 514/8 |
| 4,396,607 | 8/1983 | Lefrancier et al. ........... 424/177 |
| 4,397,844 | 8/1983 | Baschang et al. ............ 424/177 |
| 4,401,659 | 8/1983 | Lefrancier et al. ........... 424/177 |
| 4,406,890 | 9/1983 | Tarcsay et al. .............. 424/177 |
| 4,414,204 | 11/1983 | Tarcsay et al. .............. 424/177 |
| 4,427,659 | 1/1984 | Le Francier et al. .......... 424/177 |
| 4,435,386 | 3/1984 | Ribi et al. ................... 424/177 |
| 4,436,727 | 3/1984 | Ribi ........................... 424/177 |
| 4,436,728 | 3/1984 | Ribi et al. ................... 424/177 |
| 4,446,128 | 5/1984 | Baschang et al. ............ 424/88 |
| 4,461,761 | 7/1984 | Lefrancier et al. ........... 424/177 |
| 4,505,899 | 3/1985 | Ribi et al. ................... 514/8 |
| 4,505,900 | 3/1985 | Ribi et al. ................... 514/2 |
| 4,515,891 | 5/1985 | Yokogawa et al. ........... 435/69 |
| 4,522,811 | 6/1985 | Eppstein et al. .............. 514/2 |
| 4,545,932 | 10/1985 | Takase et al. ............... 530/322 |
| 4,770,874 | 9/1988 | Allison ....................... 424/88 |

OTHER PUBLICATIONS

N. C. Phillips et al., *Cancer Res.*, 45, 128 (1985).
T. Andronova et al., *Chem. of Pept. and Prot.*, 1, 343 (1982).
M. Guinand et al., *Eur. J. Biochem.*, 143, 359 (1984).
W. R. Hargreaves et al., *Biochem.*, 176, 3759(1978).
V. T. Ivanov et al., "Synthesis, Structure and Biological Properties of Glycopeptides Containing the N-Acetyl-Glucosaminyl-O-($\beta$1-4)-N-Acetylmuramyl Disaccharide Unit", Proceedings of the Sixteenth Peptide Symposium, Brunfeldt K. ed., Striptor Copenhagen, 1981, pp. 494-500.
E. Ribi et al., *Ann. N.Y. Acad. Science*, U.S.A., 277, 228 (1976).
G. Sava et al., *Cancer Immunol. Immunother.*, 18, 49 (1984).
G. Sava et al., *Cancer Immunol. Immunother.*, 15, 84 (1983).
S. Sone et al., *Cancer Immunol. Immunother.*, 12, 203 (1982).

Primary Examiner—Lester L. Lee
Attorney, Agent, or Firm—Merchant, Gould, Smith, Edell, Welter & Schmidt

[57] ABSTRACT

The present invention provides a novel lipophilic dissacharide-tripeptide derivative of the known base compound muramyl dipeptide (MDP). The compound of the invention is preferably encapsulated into multilamellar liposomes, which can be formed from phosphatidyl choline and phosphatidyl glycerol. The compound is effective in activating human monocytes with subsequent destruction of tumor cells. The compound is also nontoxic in dosages well exceeding anticipated human dosages.

14 Claims, No Drawings

1

COMPOSITION FOR MACROPHAGE ACTIVATION

FIELD OF THE INVENTION

The present invention provides a novel lipophilic disaccharide-tripeptide compound having improved anti-tumor efficacy, and a liposome encapsulated composition comprising said compound.

BACKGROUND OF THE INVENTION

Intact microbial agents ar known to have antitumor effects in both experimentally induced and human malignancies. The active components, consisting of the peptidoglycan cell wall skeleton and trehalose dimycolate, have been isolated from mycobacteria. These active components, especially when attached to mineral oil or squalene, are known to be as active as the intact microbial agents. See, for example, E. Ribi, et al, Ann. NY Acad. Science, U.S.A., 277, 228–236 (1976).

The cell wall skeleton of Nocardia rubra (N-CWS) is also known to activate macrophages. Given intravenously, oil-attached N-CWS can cure some rats with experimental pulmonary metastases. See, for example, S. Sone, et al, Cancer Immunology Immunotherapy, 12, 203–209 (1982). Smaller, water soluble monomeric units of the cell wall peptidoglycans have been demonstrated to be adjuvant active. Adjuvants are compounds causing non-specific stimulation of the immune system of a human or other mammal which result in an increased production of antibodies and in an enhancement of the protective reaction of the organism, e.g., against infection. Such monomeric units have also shown antitumor activity when given intravenously, for example, in mice bearing the Lewis lung carcinoma or the MCA mammary carcinoma. See, for example, Sava, G. et al, Cancer Immunology Immunotherapy, 15, 84–86 (1983).

The active components of these organisms have been isolated, purified and synthesized. These components are glycopeptides which constitute a broad class of organic compounds which include a sugar part and a peptide part. Glycopeptides found in the cell are known to retain not only adjuvant activity, as evidenced by their ability to increase the antibody response, but also possess antitumor activity, as evidenced by their ability to activate macrophages to become cytotoxic and destroy tumor cells. For example, muramyl dipeptides (MDP), (e.g. N-acetylmuramyl-L-alanyl-D-isoglutamine) and a large number of MDP derivatives are known to have antitumor macrophage activation properties.

Both the intact microbial agents and many MDP compounds have shown an undesirable level of toxicity. Intact microbial agents, used alone or in an oil-in-water emulsion, such as Freund's adjuvant, can cause an increased sensitivity to histamine, granuloma formation and hyperplasia of the liver and spleen. Toxic reactions due to administration of certain MDP compounds has included fever and generalized vasculitis when given in repeated doses.

Both the in vitro and in vivo antitumor activity of many mono-and disaccharide-peptides is increased by their incorporation into liposomes. Lipophilic derivatives of immunogenic and/or antitumor agents are known, and are useful for efficiently incorporating useful agents into liposomes for targeting macrophages and activating macrophages to the cytotoxic state.

Therefore, there is a need for a novel glycopeptide compound which has improved adjuvant and/or antitumor activity, which is readily incorporated into liposomes, and which is nontoxic in dosages well exceeding anticipated effective human dosages.

SUMMARY OF THE INVENTION

The present invention provides a novel lipophilic disaccharide-tripeptide derivative of the known base compound muramyl dipeptide (MDP). The compound of the invention is preferably encapsulated into multilamellar liposomes, which can be formed from, for example, phosphatidyl choline and phosphatidyl glycerol. The compound is effective in activating human monocytes with subsequent destruction of tumor cells. The compound is also nontoxic in dosages well exceeding anticipated human dosages.

The compound of the invention has the formula (I):

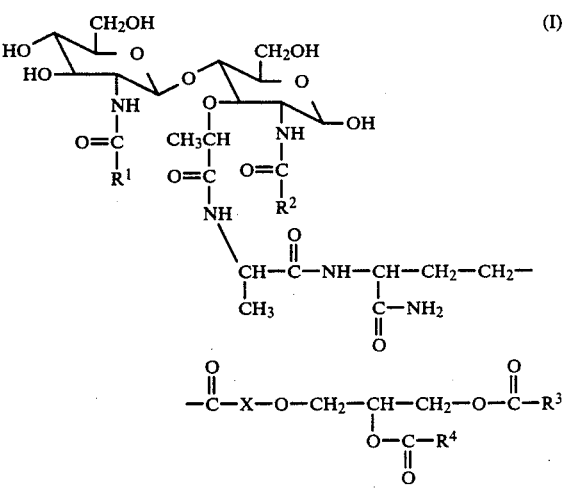

wherein $R^1$ is ($C_1$ - $C_5$) alkyl, $R^2$ is ($C_1$ - $C_5$) alkyl, $R^3$ and $R^4$ are individually ($C_6$ - $C_{30}$) alkyl groups comprising about 0–4 double bonds. X is a peptidyl residue, e.g., an amino acid residue of general formula:

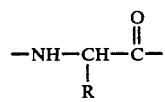

Preferably X is an L-alanine residue of the formula:

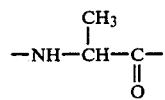

The pharmaceutically-acceptable salts thereof, and a liposome comprising a compound of the above formula are also within the scope of the invention. Although with a few exceptions, naturally occurring proteins contain only the L-enantiomorphs of their component amino acids, the D-enantiomorphs can also be used in the present compositions as can DL-mixtures of amino acids.

DETAILED DESCRIPTION OF THE INVENTION

Chemical Structure of the Novel Compound

The compound of the present invention (Compound I) is a novel lipophilic disaccharidetripeptide derivative of the known base compound muramyl dipeptide (MDP).

Compound I includes a glucosamine (Glc) derivative having an acyl group with about 2 to 6 carbons attached to the nitrogen. Preferably, the acyl group has 2 carbons (acetyl) forming N-acetylglucosamine (GlcNAc).

The N-acylglucosamine moiety is attached to an N-acylmuramyl moiety. The acyl functionality attached to the nitrogen of the muramyl group has about 2 to 6 carbons, preferably 2 carbons, forming an N-acetyl muramyl group. The alternating disaccharide GlcNAc-MurNAc is a naturally occurring dissacharide, found in bacterial cell walls as part of a polymeric glycopeptide. See, U.S. Pat. No. 4,395,399.

The disaccharide moiety of Compound I N-acylglucosamine-N-acylmuramate, is bonded to the N-terminus of a tripeptide moiety through the lactyl ether linkage at the number 3 position on the muramyl group. The tripeptide moiety comprises the dipeptide, L-alanyl-D-isoglutamine, which is found in the naturally occurring monomeric unit of the bacterial peptidoglycan, N-acetylmuramyl-L-alanyl-D-isoglutamine. The third amino acid of the tripeptide moiety, represented as X in the formula of Compound I above, is any peptidyl residue, and is preferably L-alanine. Thus, the preferred tripeptide moiety is, L-alanine-D-isoglutamine-L-alanine (L-Ala-D-isoGln-L-Ala). The disaccharide-tripeptide portion of the novel compound may be referred to as N-acylglucosaminyl-N-acylmuramyl-tripeptide.

The lipophilic end of the compound of the invention is comprised of a derivative of glycerol substituted with two acyl groups, individually having between 7 and 31 carbons, preferably 12–23 carbons, and about 0 to 4 double bonds, preferably about 0–1 double bonds. Preferably both acyl groups have 16 carbons [$C_{16}$] to form a dipalmitoyl-glycerol derivative. The remaining -OH of the glycerol is attached to the C-terminus of the terminal amino acid, X, of the tripeptide moiety.

The novel compound of the present invention can generally be described as an N-acylglucosaminyl-N-acylmuramyl-tripeptide-diacyl-glycerol compound. Preferably the compound is N-acetylglucosaminyl-N-acetylmuramyl-L-alanine-D-isoglutamine-L-alaninedipalmitoylglycerol (GlcNAcMurNAc-L-Ala-D-isoGln-LDPG or GMTP-DPG).

The Compound I may also be used as a pharmaceutically acceptable salt of the formula above. Such salts include the amine salts which are derived from organic acids such as citrate, lactic, malic, methane sulfonic, p-toluene sulfonic and the like; as well as inorganic acids such as hydrochloric acid, sulfuric acid, phosphoric acid, and the like. Salts such as (lower) alkyl sulfate and halides can also be used. For isolation or purification of the compound, pharmaceutically-unacceptable salts may also be used. However, only the pharmaceutically-acceptable, non-toxic salts can be used thereapeutically, and are therefore preferred.

Liposomes

The liposomes are generally produced from phospholipids or other lipid substances and are formed of mono or multilamellar hydrated liquid crystals. They are customarily used in dispersions in an aqueous carrier medium. The use of liposomes incorporationg Compound I results in an increase in the adjuvant and anti-tumor activity. Also, an increase in humoral and/or cellular mediation immune responses is often observed. Thus, Compound I is preferably included in liposomes.

There are a number of conventional procedures to form liposomes. Any non-toxic, physiologically acceptable and metabolizable lipid, capable of forming liposomes, can be used. The most usual lipids are the phospholipids, and notably the phosphatidyl-cholines (lecithins), both natural and synthetic. Phospholipids may also be used, for example, the phosphatidyl-serines, the phosphatidyl-inositides or the sphingomyelines. Other lipids can also be used, which have been described, for example, by W. R. Hargreaves and D. W. Deamer (Conference on Liposomes and Their Uses in Biology and Medicine, Sept. 14–16, 1977, *New York Acad. Sci.*) and in *Biochem.*, 18, 3759, (1978).

Traditional techniques and apparatus can be employed to form the liposomes according to the invention. These techniques are described in, for example, Chapter IV of the work entitled "Methods in Cell Biology", edited by David M. Prescott, Volume XIV, 1976, Academic Press, New York, page 33 et seq.

Another method of encapsulating the active Compound I into a liposome involves casting a film of phospholipid (with or without a charged lipid) by evaporation from a solution in an organic solvent, and then dispersing the film in a suitable aqueous medium. In the case of lipid-soluble, biologically active compounds, that is, those which associate with the lipid layers rather than with the aqueous phase of the liposomes, the compound is usually cast as a film together with a phospholipid, using a common organic solvent. In the case of water-soluble, biologically active compounds, the compound is typically encapsulated in liposomes by dispersing a cast phospholipid film with an aqueous solution of the compound. The encapsulated compound is then separated from the free compound by centrifugation, chromatography or some other suitable procedure.

The lipophilic end of Compound I enhances its incorporation into liposomes. Compound I is preferably incorporated into a liposome having a bilayer membrane consisting essentially of 1-palmitoyl-2-oleoyl-phosphatidyl choline (PC) and dioleoyl phosphatidyl glycerol (PG) in a weight ratio of about 5-1:1, preferably about 7:3. These compounds are commercially available from Avanti Polar Lipids, of Pelham, Ala.

Preferred methods which can be used to encapsulate Compound I into a liposome are described in U.S. Pat. No. 4,370,349 which is incorporated herein by reference. The methods comprise either (1) dissolving the necessary substances in a suitable solvent and then freeze-drying the solution, storing the resulting freeze-dried mixture, and, when desired, reconstituting it into an aqueous liposome preparation, or (2) preparing an aqueous liposome preparation by any known method and freeze-drying the preparation. When desired, the freeze-dried product can be made up into an aqueous liposome preparation. The freeze-dried mixtures disperse easily when shaken with an aqueous medium, and use of the freeze dried liposomes results in liposome preparations having a narrower size distribution than a corresponding preparation obtained by dispersing a cast film. This is advantageous to the reproducibility of the therapeutic effect of liposome preparations. Generally, the compositions in the form of the liposomes can contain, in addition to Compound I any constituents: stabilizers, preservatives, excipients or other active substances capable of being used in the injectable solutions or emulsions presented previously for administration of muramyl-peptide compounds.

Delivery

Compound I, preferably incorporated into liposomes, may be used for their adjuvant or anti-tumor activity, and may be administered orally or parenterally, preferably by injection.

The invention relates in particular to medicinal adjuvant and anti-tumor compositions, containing Compound I in association with a pharmaceutically acceptable carrier vehicle. Compositions of this type which are particularly preferred are constituted b the injectable solutions containing an effective dose of the product of the invention. Sterile solutions in an aqueous, preferably isotonic liquid, such as saline isotonic solutions or isotonic solutions of glucose, are advantageously used for this purpose. A simple solution in distilled water can also be used. It is also possible to use injection media containing an oily phase, especially water-in-oil emulsions. Such emulsions are obtained in particular with metabolizable vegetable oils, such as are described in the French Patent Application No. 75-04003. That French patent application corresponds to the U.S. copending patent application Ser. No. 656,738 of Audibert et al., filed on Feb. 9, 1976, based on said French priority patent application Ser. No. 75-04003. The preferred carrier vehicle is the freeze-dried liposomes described above.

The adjuvant and anti-tumor compositions of the invention may also be administered in various forms, by using for this purpose vehicles suitable for the selected method of administration. For example, unit dosage forms will be used in the form of cachets, compressed tablets or hard or soft gelatine-capsules, for oral administration, and aerosols or gels for the application to mucous membranes.

The compositions may also be in lyophilized form so as to permit the extemporaneous preparation of the adjuvant and anti-tumor compositions. A pharmaceutically advantageous form comprises unit doses of about 200 micrograms to 10 milligrams of Compound I per meter$^2$ of body surface area.

Manufacture

Compound I, for example, 4-0-[2-acetamido-2-deoxy-$\beta$-D-glucopyranosyl]-2-acetamido-2-deoxy-3-0-[D-2-propanoyl-L-alanyl-D-isoglutaminyl-L-alanine2,3-dipalmitoyl-sn-glycerol]-D-glucopyranose, (GlcNAc-MurNAc-L-Ala-D-isoGln-L-Ala-DPG), may be prepared from commercially available materials, in about nine major steps. The steps do not necessarily have to be performed in the order described as will become apparent from the description herein below.

The first step involves the preparation of a blocked amino acid-diacyl glycerol. This is the lipophilic portion of Compound I attached to the C-terminus of the amino acid residue, X, which is preferably an L-alanine residue. For example, in a preferred embodiment this residue would be blocked-L-alanine-2,3-dipalmitoyl-sn-glycerol.

The blocked amino acids or peptides employed as starting materials in the synthesis are either commercially available in the blocked form or are obtained by known methods of peptide chemistry. Blocking groups or protecting groups that can readily be split off are those known from peptide and sugar chemistry. For hydroxy groups the following are suitable examples: acyl radicals, for example lower alkanoyl radicals, such as acetyl, aroyl radicals, such as benzoyl, and especially radicals derived from carbonic acid derivatives, such as benzyloxycarbonyl or lower alkoxycarbonyl, or alkyl, especially tert-butyl, benzyl, optionally substituted by nitro, (lower) alkoxy or by halogen, triphenylmethyl or tetrahydropyranyl, each optionally substituted by halogen or by lower alkoxy such as methoxy, or optionally substituted alkylidene radicals that bond the oxygen atoms in the 4- and 6-position. Such alkylidene radicals are preferably a lower alkylidene radical, e.g., the methylidene, isopropylidene or propylidene radicals, or alternatively an optionally-substituted benzylidene radical.

For blocking C-terminal carboxy groups, suitable moieties include tert-butyl, benzyl or benzhydryl. For protection of free amino groups, tert-butyloxycarbonyl or benzyloxycarbonyl groups can be used.

These blocking groups can be cleaved in a manner known in the art, such as acid hydrolysis. Benzyl or benzylidene radicals also can be removed by hydrogenolysis, for example using hydrogen in the presence of a noble metal catalyst, such as a palladium or platinum catalyst.

The second step in the preparation of the compound of the invention involves removal of the blocking group from the amino acid to form X-diacyl-glycerol, where X is an amino acid residue as described above, preferably L-alanine. For example, a preferred component is L-alanine-2, 3-dipalmitoyl-sn-glycerol (L-Ala-DPG).

The third step involves isolation of the disaccharide moiety from a suitable bacteria, for example *Micrococcus lysodeikticus* (dried cells are commercially available from Sigma Chemical Co., St. Louis, Mo.). The disaccharide that is obtained is N-acetylglucosaminyl-N-acetylmuramate. The isolation of this disaccharide from a biomass of *Micrococcus lysodeicticus* is known and described in the literature. It involves enzymatic hydrolysis of the biomass of *Micrococus lysodeikticus* by means of trypsin and lysozyme and a further purification in a column packed with Dowex ® 1X8 (CH$_3$COO$^-$ form) 200–400 mesh (Hoshino 0., Zenavi U., Sinay P., Jeanloz R. W., *J. Biol. Chem.* 247, No. 2, 381 (1972); and Sharon N., Osawa T., Flowers H. M., Jeanloz R. W, *J. Biol. Chemistry*, 241, 223 (1966). Also, see, U.S. Pat. No. 4,427,659, which is incorporated herein by reference.

In the disaccharide isolated above, R$^1$ and R$^2$ are both —CH$_3$, forming acetyl groups on both the muramyl and glucosamyl functionalities. The analogous compounds, where R$^1$ and R$^2$ are individually C$_2$ to C$_6$ alkyl groups, can be prepared by methods known in the art. For example, the acetyl group can be hydrolyzed by a strong base, for example, as described in P. H. Gross and R. W. Jeanloz (J. Org. Chem. 1967, 32, 2761). Then an acylating agent, corresponding to the R$^1$ or R$^2$ which is desired to be introduced, such as an acid anhydride or chloride, may be used to attach the desired R$^1$ or R$^2$ group to the muramyl or glucosaminyl functionality.

The next step involves the preparation of the dipeptide alanine-isoglutamine which is blocked on both ends. BOC-L-alanyl-D-isoglutamine, commercially available from United State Biochemical Co of Cleveland, Ohio (USBC), must be treated in a manner known in the art to terminate the C-terminus isoglutamine residue with a suitable blocking agent, such as a benzyl ester (-OBn). BOC refers to N-tert-butoxycarbonyl. Thus, BOC-L-Ala-D-isoGln-OBn is preferably formed.

The next step involves the removal of the blocking group from the alanine by a known method to form, for example, L-Ala-D-isoGln-OBn. The next step involves coupling the N-acylglucosamine-N-acylmuramyl functionality with the alanine-isoglutamine moiety. The condensation reaction is conducted in an inert solvent medium, preferably in the presence of a condensation agent, such as Woodward's Reagent K (N-ethyl-5-phenylisoxazolium-3'-sulphonate), at a temperature of about 0° to 25° C. in one stage. See, U.S. Pat. No. 4,395,399.

The next step involves removal of the blocking group by conventional means to form the unblocked disaccharide-dipeptide, for example, 4-0-[2-acetamido2-deoxy-β-D-glucopyranosyl]-2-acetamido-2-deoxy-3-0-[D-2-propanoyl-L-alanyl-D-isoglutamine]-D-glucopyranose (GlcNAcMurNAc-L-Ala-D-isoGln).

The final step involves the coupling of the GlcNAc-MurNAc-L-Ala-D-isoGln with the amino acid-diacyl glycerol component by conventional techniques to form the Compound I.

Compound I is preferably encapsulated into liposomes as described herein above. Preferably the compound of the invention is combined with phosphatidyl choline and phosphatidyl glycerol. Typically the phospholipids are dissolved in tert-butanol at a concentration of about 100 mg per ml. Appropriate amounts of the PC and PG in tert-butanol are mixed to give a weight ratio of about 7:3. Compound I is weighed out and added to a given volume of the lipids to give a final concentration of, for example, about 1 mg per 5 ml. The material is then passed through a filter and the composition is dispensed into vials. The vials are frozen, typically at −20° C. and then lyophilized typically at about 20° C. for 18 hours. The vials are then sealed under an inert gas, such as argon.

The present invention is further described by way of the following non-limiting examples:

EXAMPLE 1

Preparation of BOC-L-Ala-DPG

In a 25 ml round-bottom flask (RBF) was placed 208.64 mg (1.103 mMol) of BOC-L-alanine, 570.0 mg (1.002 mMol) of 1,2-dipalmitoyl-sn-glycerol (Sigma), 63.14 mg (0.517 mMol) of 4-dimethylaminopyridine (DMAP) (Aldrich Chemical Co., Milwaukee, Wis.), and 230.04 mg (1.200 mMol) of 1-ethyl-3-(3-dimethylaminopropyl)carbodiimide hydrochloride (EDCl). BOC is the abbreviation for N-tert-butoxycarbonyl, a blocking group. Methylene choride ($CH_2Cl_2$) was added bringing the final volume to 14 ml. The mixture was stirred in an ice-water bath for 1 hour, then at room temperature (RT) overnight.

After stirring overnight the solvent was removed on a rotary evaporator under aspirator vacuum to yield a white solid, which was partitioned between 20 ml of ethyl acetate (EtOAc) and 10 ml of water. The water layer was extracted with another 20 ml of EtOAc. The organic fractions were combined and treated with 2×20 ml of saturated aqueous sodium bicarbonate followed by 2×20 ml of water and then dried over $Na_2SO_4$. The solvent was removed on a rotary evaporator to yield 648 mg (87%) of BOC-L-Ala-DPG as a white solid.

EXAMPLE 2

Preparation of L-Ala-DPG 630 mg (0.85 mMol) of BOC-L-Ala-DPG was dissolved in 15 ml of $CH_2Cl_2$ to which was added 5.0 ml of trifluoroacetic acid (TFA). The solution was stirred at room temperature for 2 hours, then concentrated to dryness on a rotary evaporator to yield a tan oil that was dissolved in 10 ml of hexane and concentrated to dryness on a rotary evaporator. The process was repeated several times to remove the last traces of TFA. This material was then dried under high vacuum to yield 606.7 mg of L-Ala-DPG trifluoroacetate as an off-white solid.

EXAMPLE 3

Preparation of the GlcNAcMurNAc 15.0 grams of dried cells of Micrococcus lysodeikticus (commercially available from Sigma Chemical Co., St. Louis, Mo.), was suspended in 200 ml of distilled water and disrupted by stirring at high speed with 250 g of 0.1 mm glass beads for 90 minutes at 4° C. The cell wall skeletons (CWS) were removed from the glass beads by decantation and then centrifuged at 1200×g for 30 minutes. The supernatant was removed from the pellet (intact cells), then centrifugation at 10,000×g for 50 minutes. The supernatant was removed and the resulting pellet (crude CWS) was washed 3 times by suspension in 100 ml of distilled $H_2O$ and centrifugation at 10,000×g for 70 minutes. The resulting pellet was suspended in 150 ml of distilled water and then placed in a boiling water bath for 30 minutes.

After cooling to ambient temperature, the resulting slurry was centrifuged at 10,000×g. The supernatant was removed and the pellet slurried in 60 ml of 0.05 M ammonium acetate buffer (pH 7.60). The resulting slurry was treated with 10.0 mq of porcine pancreas trypsin (Sigma, 14,600 BAC units/mg), and incubated at 37° C. for 20 hours. After several washes with distilled $H_2O$, the CWS pellet was slurried in 60 ml of 0.05 M ammonium acetate buffer (pH 6.30), treated with egg-white lysozyme (Sigma, 56,000 units/mg, 10.0 mg) and incubated at 37° C. for 19 hours.

The crude preparation was dialysed to remove the enzymes and undigested cell walls. Final purification was achieved by ion exchange chromatography on Dowex®-1 (acetate form) by elution with an acetic acid gradient. The column fractions were pooled based on UV absorbance and thin layer chromatography (TLC) (silica gel, 50:39:8:3 $CHCl_3/CH_3OH/H_2O/N-H_4OH$, 5% $H_2SO_4/EtOH$ and heating). Positive identification of the disaccharide product was obtained from colorimetric analysis of muramic acid and total hexosamines, and fast atom bombardment mass spectrometry. Yields were 120 mg GlcNacMurNac from 15 g of dried cells.

EXAMPLE 4

Preparation of BOC-L-Ala-D-isoGln-OBn

Benzyl alcohol (77.0 mg, 0.71 mMol), DMAP (33.0 mg, 0.27 mMol), and BOC-L-alanyl-D-isoglutamine (159.0 mg, 0.50 mMol) were dissolved in 5 ml of $CH_2Cl_2$ and 2 ml of DMF. This solution was cooled in an ice-water bath to 4° C., treated with EDCI (118.0 mg, 0.61 mMol) and stirred at 4° C. for 30 minutes, then at room temperature for 15 hours. After removing the solvents in the rotary evaporator, the residue was partitioned between 20 ml of EtOAc and 10 ml of water. The layers were separated and the aqueous layer extracted with another 20 ml of ethyl acetate. The organic fractions were combined, then successively extracted with saturated $NaHCO_3$ (2×20 ml) and $H_2O$ (2×20 ml). After drying over sodium sulfate, the solvent was removed on the rotary evaporator leaving a waxy solid, which was recrystallized from EtOAc-petroleum ether to yield 141 mg (69%) of BOC-L-Ala-D-isoGln-OBn as a white fluffy solid.

EXAMPLE 5

Preparation of L-Ala-D-isoGln-OBn

BOC-L-Ala-D-isoGln-OBn (120 mg, 0.294 mMol) was treated with 10 ml of 1N HCl/HOAc and the resulting solution stirred at RT for 2 hours. The solvent was then removed on the rotary evaporator to yield a colorless oil, which was taken up in 3 ml of methyl alcohol, then precipitated by the dropwise addition of 20 ml of diethyl ether. After stirring for 1 hour at RT, the product was collected on a filter, washed with ether, then dried under high vacuum to yield 88 mg of the hydrochloride salt of L-Ala-D-isoGln-OBn as a white solid.

EXAMPLE 6

Coupling of GlcNAcMurNAc with -L-Ala-D-IsoGln-OBn

A total of 200 mg of GlcNAcMurNAc (MW 496.47, 0.405 mMol) was dissolved in 15 ml of dimethylformamide (DMF) and then treated with 0.95 ml of a solution containing 42.94 mg/ml of triethylamine (TEA) in DMF (0.403 mMol). The solution was cooled with magnetic stirring in an ice bath and then treated with 139.63 mg (95% pure, 0.524 mMol) Woodward's Reagent K. The slurry was then stirred in an ice-water bath for 1 hour, then at room temperature for 10 minutes. Then a solution containing 152.3 mg (0.443 mMol) of the HCl salt of the L-Ala-D-isoGln-OBn in 8.0 ml of DMF to which was added 1.05 ml (0.443 mMol) of the TEA/DMF solution was added via a pressure equalizing funnel over a period of 10 minutes. The solution was stirred at RT for 18 hours and then allowed to stand for an additional 96 hours. The reaction was followed during this time by TLC and allowed to go as far as possible to completion.

The DMF was removed in a rotary evaporator under high vacuum (approximately 50 microns) at 25° C. to yield a reddish oil that was further dried under high vacuum.

The oil was taken up in 5 ml of H2O and applied to a 1.7×7 cm column of Dowex ®1 X 8 (200-400 mesh, acetate form). The column was washed with 50 ml of H2O and the entire colorless eluate applied to a 1.7 ×7 cm column of Amberlite ®IR-120 P resin (16-20 mesh, H + form), The column was washed with 50 ml of H20 and the eluate and washings were combined. This material was taken to dryness in a rotary evaporator under aspirator vacuum at 25° C. to yield a colorless oil. This was dried under high vacuum (50-75 microns) overnight during which time it solidified to a glassy solid. This was taken up in 20 ml of H2O and lyophilized to yield 181 mg of GlcNAcMurNAc-L-Ala-D-isoGln-OBn as a snow white fluffy solid.

EXAMPLE 7

Preparation of GlcNAcMurNAc-L-Ala-D-isoGln 170 mg of the protected material prepared in Example 6 was dissolved in a solution of H2O (30 ml) and acetic acid (1.0 ml). The solution was added to 100 mg of 5% Pd/C (by weight of the palladium, C is powdered charcoal, from Matheson, Coleman, and Bell of Norwood, Ohio) in a 500 ml Parr hydrogenation bottle and hydrogenated at 20 psig for 24 hours. The catalyst was removed and washed with water (3×10 ml), and the filtrate and washings were combined and lyophilized to yield 150 mg (100%) of GlcNAcMurNAc-L-Ala-D-isoGln as a white solid. The product was further dried under high vacuum for 48 hours then tightly capped and stored at 4° C.

EXAMPLE 8

Coupling of GlcNAcMurNAc-L-Ala-D-Isoglutamine to L-Ala-DPG to yield GlcNAcMurNAc-L-Ala-D-isoGln-L-Ala-DPG 1-Hydroxybenzotriazole (HOBT) (31.35 mg, 0.232 mMol) and EDCI (44.26 mg, 0.231 mMol) were placed in a 50 ml-RBF. To this was added a solution containing the disaccharide dipeptide as prepared in Example 7 (139.13 mg, 0.20 mMol) in 7 ml DMF and 5 ml CH2Cl2. The resulting solution was stirred at RT for 30 minutes.

A triethylamine solution was prepared by dissolving 202 mg (0.28 ml) of TEA in DMF and adjusting the final volume to 10 ml.

L-Ala-DPG (150.8 mg, 0.20 mMol) was dissolved in 1 ml of CH2Cl2 DMF (1 ml) was added, followed by 1 ml of the TEA solution. The resulting solution was added to the activated disaccharide dipeptide solution, the vessel was securely capped and stirred for 72 hours.

The reaction was followed by TLC and stopped at 72 hours. The reaction mixture was then split into two portions, one of 5 ml, the other of 10 ml. These samples were concentrated to dryness on a rotary evaporator at room temperature under high vacuum. They were then further dried in a desiccator for 24 hours during which time both samples dried to yellow-orange solids.

For purification, the smaller portion was partitioned between 25 ml H2O and 25 ml EtOAc. The layers were separated, and the organic layer was extracted with 2×10 ml of H2O and the washes added to the aqueous layer. The aqueous fraction was then washed with 25 ml of EtOAc, the layers were separated and the organic fractions combined. The aqueous layer was concentrated to half volume on a rotary evaporator and the remainder extensively dialyzed against H2O through an Amicon YM-5 membrane at 30-35 psi.

TLC analysis of the inner dialysate showed a single spot. This material was then filtered through Whatman® #2 paper than lyophilized to yield 35 mg of a cream colored solid.

EXAMPLE 9

Preparation of GMTP-DPG

BOC-L-Ala-DPG (II) - 1,2-Dipalmitoyl-sn-glycerol (Sigma, 2.845 g, 5.0 mMol), BOC-L-alanine (USBC, 966 mg, 5.1 mMol), and 4-dimethylaminopyridine (DMAP) (Aldrich, 357 mg, 2.93 mMol) were dissolved in 50 ml of methylene chloride (CH2Cl2) 1-Ethy.l-3-(3-dimethylaminopropyl) carbodiimide hydrochloride (EDCI) (Sigma 1.174 g, 6.12 mMol) was added, and the solution was stirred at room temperature (RT) for 17 hours. After removal of the solvent on the rotary evaporator, the residue was partitioned between 150 ml of ethyl acetate (EtOAc) and 75 ml of H2O, the layers separated and the organic layer extracted with saturated aqueous sodium bicarbonate (3 x 50 ml), then with H2O (3×75 ml). After drying over sodium sulfate, the solvent was removed on the rotary evaporator and the residue further dried under high vacuum to yield 3.59 g (97%) of product as a slightly off-white solid.

A thin layer chromatogram (TLC) (silica; CHCl$_3$/CH$_3$OH/H$_2$O, 130:45:7; HCl spray, then ninhydrin) of the product revealed a single spot of Rf 0.95.

L-Ala-DPG (III) - The protected alanine ester (II) (2.50 g, 3.38 mMol) was dissolved in 75 ml of CH$_2$Cl$_2$, then treated with 25 ml of trifluoracetic acid (TFA). After standing at room temperature for 2 hours, the solvents were removed on the rotary evaporator to leave a tan oil that was repeatedly taken up in 20 ml portions of hexane then concentrated to dryness on the rotary evaporator. After extensive drying under high vacuum, 2.44 g (95.7%) of Compound III was obtained as its trifluoroacetate salt.

BOC-L-Ala-isoGln-OBn (IV) - BOC-L-Ala-D-isoGln (USBC, 1.587 g, 5.0 mMol), benzyl alcohol (540.7 mg, 5.0 mMol), and DMAP (305 mg, 2.5 mMol) were dissolved in 40 ml of CH$_2$Cl$_2$ and 10 ml of N,N-dimethylformamide (DMF), and the resulting solution was cooled in an ice-water bath to 4° C. with magnetic stirring. EDCI (1.150 g, 6.00 mMol) was added, and the reaction stirred in the ice bath for 1 hour, then at room temperature for 17 hours. After removal of the solvents on the rotary evaporator, the oily residue was partitioned between 50 ml of H$_2$O and 150 ml of EtOAc, the layers separated, and the organic layer further extracted with saturated aqueous sodium bicarbonate (3×50 ml) and H$_2$O (3×50 ml). After drying over sodium sulfate, the solvent was removed on the rotary evaporator to yield a colorless oil that was further dried under high vacuum, during which it solidified to a waxy solid. Recrystallization from EtOAc-hexane yielded 1.318 g (65%) of Compound IV as a snow-white solid.

A TLC (silica; EtOAc/pyridine/acetic acid/H$_2$O, 30:2:0.6:1; HCl spray, then ninhydrin) of the product revealed a single spot of Rf 0.90.

L-Ala-D-isoGln-OBn (V) - The protected dipeptide ester IV (2.08 g, 5.10 mMol) was treated with 100 ml of 1N HCl/acetic acid, and the resulting solution was allowed to stand at room temperature for 2 hours. After removal of the solvents on the rotary evaporator and further drying under high vacuum, the product was crystallized from methanol-ether to yield 1.68 g (95.8%) of Compound V as its hydrochloride salt.

GlcNAcMurNAc (VI) - Commercially available lyophilized *Micrococcus lysodeikticus* (Sigma), in the form of dried cells was suspended (2–3% w/w) in distilled water, then disrupted with a Microfluidics Corporation laboratory Microfluidizer® (Model M-110Y). This was driven by a Powerex® GI-25 air compressor at a normal operating air pressure of 82 PSIG, which resulted in a hydraulic pressure of 19,000 PSIG. The cell walls were then isolated by differential centrifugation, then subjected to successive treatments with trypsin and lysozyme as described in Example 3. The resulting digest was then dialyzed (Amicon PM-10 membrane) to remove enzymes and large molecular weight contaminants, then purified by ion exchange chromatography on Dowex®-1 (acetate form) by elution with an acetic acid gradient. The column fractions were pooled based on UV absorbance and TLC (silica; CHCl$_3$/CH$_3$OH/H$_2$O/NH$_4$OH, 50:39:8:3; 5% H$_2$SO$_4$/CH$_3$CH$_2$OH and heating). Positive identification of the disaccharide was obtained from colorimetric analysis of muramic acid and total hexosamines and from fast atom bombardment mass spectrometry (fabs). Present yields are in the range of 2.50 g of the pure disaccharide (Compound VI) from 240 g of the dried bacterial cells.

GlcNAcMurNAc-L-Ala-D-isoGln-OBn (VII) - Prior to use, the DMF was dried over 4A molecular sieves, then distilled from ninhydrin. The triethylamine (TEA) was distilled from sodium hydroxide pellets. Woodward's Reagent K was purified by dissolving 3.0 g of the commercial material (Aldrich) in 15 ml of 1N HCl, filtration through Whatman #2 paper, then precipitation by the addition of 120 ml of acetone. After filtering and washing with 100 ml of acetone, the reagent was dried under high vacuum for several hours.

The disaccharide Compound VI (2.00 g, 4.028 mMol) was dissolved in 100 ml of DMF, treated with TEA (0.62 ml, 447.5 mg, 4.431 mMol), cooled in an ice-water bath to near 4° C., then treated with Woodward's Reagent K (95%, 1.397 g, 5.24 mMol). The resulting slurry was stirred in the ice-water bath for 1 hour, then at room temperature for 10 minutes. Then, a solution containing the dipeptide benzyl ester (V) (1.523 g, 4.43 mMol) and TEA (447.42 mg, 0.616 ml) in 50 ml of DMF was added via a pressure equalizing addition funnel over a period of 30 minutes. After the addition was completed, the reaction mixture was stirred at room temperature for a total of 120 hours, during which the progress of reaction was monitored by TLC (silica; CHCl$_3$/CH$_3$OH/H$_2$O/NH$_4$OH, 50:25:4:2; 5% H$_2$SO$_4$/CH$_3$CH$_2$OH, heat). The solvent was then removed on the rotary evaporator and the oily residue further dried under high vacuum. This was then taken up in 50 ml of H$_2$O, then applied to a 2.5×17 cm column of Dowex 1 X 8 (200–400 mesh, acetate form) and eluted with 500 ml of H$_2$O. The entire eluate was concentrated to ca. 50 ml, then applied to a 2.5×17 cm column of Dowex 50 X 8 (100 mesh, H+form) and eluted with 500 ml of H$_2$O. The eluate was concentrated to ca. 50 ml, then lyophilized to yield 2.25 g (71%) of Compound VII as a snow-white solid.

GlcNAcMurNAc-L-Ala-D-isoGln (VIII) - The disaccharide dipeptide benzyl ester (VII) (2.20 g, 2.80 mMol) was dissoved in 150 ml of H$_2$O and 3.0 ml of glacial acetic acid. To this was added 300 mg of 5% Pd/C, and the resulting slurry was hydrogenated at room temperature and 40 PSIG for 40 hours. The catalyst was then removed by filtration through a Celite pad, washed with H$_2$O (3×10 ml), and the filtrate and washings combined, concentrated to ca. 50 ml, then passed through a 1 ml column of Detoxi-Gel ® (Pierce) at a flow rate of 8 ml/hr. The column was washed with 10 ml of H$_2$O, and the eluate and washings were combined, then lyophilized to yield 1.86 g (95.5%) of Compound VIII as a white powder.

GlcNAcMurNAc-L-Ala-D-isoGln-L-Ala-DPG (IX) -The DMF and TEA used in this preparation were purified as described in the preparation of VII. The disaccharide dipeptide VIII (1.531 g, 2.20mMol) was dissolved in 70 ml of DMF, then diluted with 50 ml of CH$_2$Cl$_2$ To this was then added 1-hydroxybenzotriazole (HOBT) (Aldrich, 387.4 mg, 2.53 mMol) and EDCI (485 mg, 2.53 mMol), and the resulting solution was stirred at room temperature for 1 hour. Then, a solution containing 1.659 g (2.2m Mol) of the ester (II) and 225 mg (0.31 ml, 2.20 mMol) of TEA in 20 ml of CH$_2$Cl$_2$ was added dropwise over a period of 5 min. The resulting solution was stirred at room temperature for 24 hours, then treated with an additional 100 mg of EDCI and stirred for another 48 hours. The solvents were removed on the rotary evaporator and the oil residue further dried under high vacuum for several hours, during which it solidified to a yellow waxy material.

This was then washed three times by suspension in 150 ml-portions of EtOAc and centrifugation at 200× g. After drying under high vacuum, the pellet was suspended in 1000 ml of distilled H$_2$O, then extensively dialyzed against distilled H$_2$O in a Amicon ultrafiltration cell through a Amicon YM-10 membrane. The inner dialysate was then diluted to 2000 ml with distilled H$_2$O, filtered through a triple layer of paper (Labconco Corp. #A-754448), concentrated to ca. 600 ml on the rotary evaporator, and lyophilized to yield 1.60 g of Compound IX as a white, electrostatic powder.

For final purification, 52.8 mg of the above product was dissolved in 1.0 ml of CHCl$_3$/CH$_3$OH/H$_2$O, 2:3:1, then applied to a 0.7×29 cm column of Sephadex LH-20-100 resin that had been swollen and packed in the same solvent. The column was eluted at a flow rate of 0.33 ml/min, and fractions of the eluate were collected and assayed by TLC (silica; CHCl$_3$/CH$_3$OH/H$_2$O/N-H$_4$OH, 50:25:4:2; 5% H$_2$SO$_4$/CH$_3$CH$_2$OH, heat). The appropriate fractions were combined, then applied directly to a 1 × 8 cm column of BioRad Cellex D resin (acetate form). This column was teen washed with 30 ml of solvent, and the combined eluate and washings concentrated to near dryness on the rotary evaporator, treated with 75 ml of H$_2$O, and lyophilized to yield 35 mg of GlcNAcMurNAc-L-AlaD-isoGln-L-Ala-DPG (GMTP-DPG) as a white powder.

Analysis for product as the dihydrate:

| C$_{65}$H$_{116}$N$_6$O$_{22}$1·2H$_2$O | | | | | |
|---|---|---|---|---|---|
| Calculated | C | 57.67 | H | 8.93 | N | 6.21 |
| Found | C | 57.89 | H | 8.58 | N | 5.91 |
| FAB-MS, m/c 1340 (M + 23), 1318M (M + 1), 1300 (M − 18 + 1) | | | | | |

EXAMPLE 10

Preparation of Liposomes

The GMTP-DPG compound (IX) was encapsulated into liposomes using the following procedure. One mg of GMTP-DPG as prepared in Example 9 was combined with 175 mg of 1-palmitoyl-2-oleoyl phosphatidyl choline (PC) and 75 mg of 1,2-dioleoyl phosphatidyl glycerol (PG), both commercially available from Avanti Polar Lipids, Pelham, Ala. The PC and PG were previously dissolved in tert-butanol at a concentration of 100 mg lipid per ml, thus giving a 7:3 weight ratio of PC:PG in tert-butanol. Tert-Butanol was then added to the 1 mg GMTP-GDP; 175 mg PC; 75 mg PG to give a final volume of 5.0 ml. The GMTP-DGP and lipid mixture was passed through a sterile millipore 0.22u filter to remove any contaminants present. The filtrate was collected in a clean, sterile, round bottom flask which was capped with aluminum foil after filling. Five ml of the filtered mixture containing 1 mg of GMTP-DPG was dispensed into 10 ml vials. After the vials were filled, they were covered with sterile rubber serum stoppers. Each of the stoppers includes a slit in one side so that air can enter and leave the vial during lyophilization and stoppering. Sterile aluminum foil was placed over the vials and the vials were transferred to the tray drying chamber of the lyophilizer. The vials were then cooled to −20° C. until the tert-butanol lipid mixture was frozen (approximately 30 to 60 minutes). The refrigeration was then turned off and the tray heater set for 10° C. The vials were then lyophilized for 18 hours. The lyophilizer containing the vials was purged with filtered sterile argon and evacuated three times. The lyophilizer containing the vials was then purged again with argon and the vials stoppered under argon at atmospheric pressure.

EXAMPLE 11

Adjuvant Activity of the Agent in Saline on Antibody Producing Cells in Combination with Particulate Antigen.

The efficacy of the compound of the invention in inducing antibody response was evaluated in an immuno-compromised model using aged Balb/c mice and in normal mice using a suboptimal dose of the immunogen.

Aged, Balb/c mice (18 months old), representing an immunodeficient animal, were immunized intraperitoneally with an optimal innoculum of 1×10$^9$ sheep red blood cells (SRBC) either alone or mixed with 0.1 mg of MDP or 0.1 mg of Compound IX. The spleen was removed on day 4 and assayed for plaque forming units.

The results (Table 1) indicated a total of 66×10$^3$ plaque forming units (PFU) per spleen for controls, 198×10$^3$ PFU per spleen for mice receiving SRBC mixed with 0.1 mg MDP and 442×10$^3$ PFU for mice receiving SRBC mixed with 0.1 mg of a compound of the invention GMTP-DPG. Similarly, young Balb/c mice were immunized intraperitoneally with a suboptimal dose of SRBC (1×10$^7$ cells) in saline or mixed with 0.01 of 0.1 mg of MDP or GMTP-DPG.

The results (Table 1) indicate that on a weight basis GMTP-DPG was 3 to 10 times more effective than MDP.

TABLE 1

| COMPARISON OF THE ADJUVANT ACTIVITY OF MDP AND GMTP-GDP (IX) | | | |
|---|---|---|---|
| AGE OF MICE | SRBC INNOCULUM | MDP (mg/mouse) | GMTP-GDP (mg/mouse) | PFU × 10$^3$ |
| 18 months | 1 × 10$^9$ | — | — | 66 |
| 18 months | 1 × 10$^8$ | 0.1 | — | 198 |
| 18 months | 1 × 10$^8$ | — | 0.1 | 442 |
| 3 months | 1 × 10$^7$ | — | — | 75 |
| 3 months | 1 × 10$^7$ | 0.01 | — | 100 |
| 3 months | 1 × 10$^7$ | 0.1 | — | 144 |
| 3 months | 1 × 10$^7$ | — | 0.01 | 184 |
| 3 months | 1 × 10$^7$ | — | 0.1 | 468 |

EXAMPLE 12

Antitumor Activity of GMTP-DPG in Saline in the Meth A Sarcoma.

BALB/C female mice, age 7 weeks, were injected subcutaneously with 1×10$^6$ Meth A tumor cells. Eight days later the animals were treated intravenously with either saline (control) or Compound IX at a dose of 1, 10 or 100 micrograms (ug). Each group consisted of 4 animals. Tumor measurements were taken every 2 days for 10 days and the mice followed for 60 days until cured or death due to tumor occurred.

The results indicated a 10 to 15% decrease in tumor size on day 6 after therapy with a single dose of 1 to 10 ug of Compound IX. A larger dose of 100 ug resulted in a 50% decrease in tumor growth at day 6 after therapy with one of four animals exhibiting complete regression of tumor.

EXAMPLE 13

Activation of Human Peripheral Blood Monocytes to the Tumoricidal State by GMTP-GDP and Liposome Encapsulated GMTP-GDP Monocyte tumoricidal activity was determined by the method of Fogler and Fidler (Fogler W. E. and Fidler I. J., *J. Immunol.*, 136:2311-2317, 1986). Briefly, human peripheral blood moncytes were isolated by gradient centrifugation on 46% Percoll. Monocytes were then cultured in suspension for 18 hours in RPMI 1640 media containing 5% human sera with or without 1.5 ug/ml of Compound IX at $1 \times 10^6$ monocytes/ml. After incubation monocytes were washed, and $1 \times 10^5$ or $5 \times 10^4$ monocytes allowed to attach to wells of a 96-well microplate for 1 hour, then the plate was washed to removenon-adherent cells; to this, $1 \times 10^4$ $I^{125}$ labeled A-375 tumor cells were added. Monocytes were cultured with tumor cells for 72 hours. At the end of the 72 hours co-culture period, the plates were washed to remove non-adherent-non-viable tumor cells and the remaining adherent viable $I^{125}$ labeled tumor cells determined by lysing the cells with sodium dodecyl sulfate and counting radioactivity in a Gamma Counter.

Activation of human peripheral blood monocytes by liposome containing Compound IX was determined by using liposomes composed of 1-palmitoyl-2-oleoyl phosphatidyl choline and 1,2 dioleoyl phosphatidylglycerol in a ratio of 7:3 by weight.

Using the tests as described in Example 12, the in-vitro efficacy of Compound II was compared to MDP. The effector:target cell ratio was 10:1. The cultures contained a final concentration of 1.0 ug/ml of MDP, Compound IX or Compound IX in liposomes. The results of these tests (Table 2) indicate that Compound IX is more effective than MDP when used as a saline suspension or when encapsulated in liposomes.

TABLE 2

| EXPERIMENT | PERCENT CYTOTOXICITY[1] | | |
|---|---|---|---|
| | MDP[2] | COMPOUND IX[3] | COMPOUND IX[4] IN LIPOSOMES[5] |
| 1 | 38% | 59% | 73% |
| 2 | 27% | 37% | 44% |

[1] Percent cytotoxicity $= \frac{A - B}{A} \times 100$ where
A = CPM in wells with control monocytes;
B = CPM in wells with treated monocytes.
[2] MDP purchased from Cal-Biochem.
[3] Compound IX at a concentration of 1 mg/ml had no detectable endotoxin as determined by LAL assay with a sensitivity of 0.06 endotoxin units per ml.
[4] Compound IX in liposomes at a concentration of 23 ug/ml had no detectable endotoxin as determined by LAL assay with a sensitivity of 0.06 endotoxin units per ml.
[5] Liposomes composed of phosphatidyl choline:phosphatidyl glycerol 7:3 molar ratio.

EXAMPLE 14

Increased effect of GMTP-DPG with LipopolYsaccharide In-Vivo.

BALB/C mice 7—8 weeks of age were injected subcutaneously with Meth A sarcoma ($1 \times 10^6$ cells) and treated intravenously on day 8 with 10 ug of lipopolysaccharide from S. typhimurium ReG 30/21 alone or combined with 1 or 10 ug of MDP or Compound IX. Tumor growth was compared on day 6 following therapy.

The animals were followed and the percent cured determined at 60 days post-injection.

The results noted in Table 3 indicate the more than additive effect of the compound with lipopolysaccharide which is more effective than the parent compound.

TABLE 3

EFFECT OF GMTP-GDP WITH LIPOPOLYSACCHARIDE ON GROWTH OF TUMORS IN MICE

| Group[1] | Percent Change in Average Tumor Area 6 Days Post Treatment | Complete Regression at Day 60 |
|---|---|---|
| Control | 191% | 0% |
| $LPS_{10}$ | 165% | 0% |
| $LPS_{10}MDP_{1.0}$ | 22% | 33% |
| $LPS_{10}Compound\ IX_{1.0}$ | −56% | 50% |
| $LPS_{10}MDP_{10}$ | −56% | 75% |
| $LPS_{10}Compound\ IX_{10}$ | −67% | 100% |

[1] The subscripts refer to the amount of compound in micrograms.

EXAMPLE 15

Acute Toxicity in Mice and Guinea Pigs

Two mice weighing between 17 and 22 grams and two guinea pigs weighing less than 400 grams were given a single intraperitoneal injection of 0.5 ml and 5.0 ml of a final clinical formulation consisting of a total of 1 mg of Compound IX, 1,740 mg of 1-palmitoyl-2-oleoyl phosphatidyl choline and 760 mg of dioleoyl phosphatidyl glycerol per 5 ml. The animals were observed daily for weight and clinical signs of distress. The results showed an initial weight loss followed by a weight gain at 7 days in guinea pigs. Mice maintain their weight and show a gain at 7 days.

EXAMPLE 16

Subacute Toxicity in Mice

A group of 10 mice were injected intravenously twice a week for four weeks with a dose of 1,320 ug per Kg of body weight. This is calculated to be equivalent to ten times an anticipated maximum human dose of 4 mg per meter squared. In the conversion from a meter squared to a kilogram basis an equivalency of 60 kilograms per 1.73 meter squared body surface area was used instead of the usual equivalency of 70 Kg body mass for a 1.73 meter squared body surface area to result in a somewhat higher dose for the toxicity studies. The results showed no weight loss over the four weeks of the test.

EXAMPLE 17

Subacute Toxicity in Rabbits

Three rabbits were treated at a dose of 132 ug per kilogram of Compound IX in liposomes per kilogram intravenously daily for 14 days. Blood obtained by cardiac puncture for clinical studies and complete autopsies for histological evidence of toxicity were performed on day 15. Blood was obtained be ear vein and by cardiac puncture on three control rabbits.

The results of this study showed no pathological evidence of toxicity. Review of the blood chemistries from the treated rabbits in comparison to the controls revealed a single rabbit with a significant increase in the creatinine phosphokinase. This abnormal value is believed related to the trauma of the cardiac puncture as evidenced by the increase in the creatinine phosphakinase in the control animals following cardiac puncture.

The invention has been described with reference to various specific and preferred embodiments and techniques. However, it should be understood that many variations and modifications may be made while remaining within the spirit and scope of the invention.

What is claimed is:

1. A compound of the formula:

(I) [structural formula of compound]

wherein $R^1$ is ($C_1$-$C_9$), $R^2$ is ($C_1$-$C_5$) alkyl and $R^3$ and $R^4$ are individually ($C_6$-$C_{30}$) alkyl groups having about 0–4 double bonds, X is an L-alanine or D-alanine residue; and the pharmaceutically-acceptable salts thereof.

2. The compound of cliam 1 wherein $R^1$ is $CH_3$.

3. The compound of claim 2 wherein $R^2$ is $CH_3$.

4. The compound of claim 1 wherein X is an L-alanine residue.

5. The compound of claim 1 wherein $R^3$ and $R^4$ are individually ($C_{12}$-$C_{23}$) alkyl groups comprising about 0–1 double bonds.

6. The compound of claim 5 wherein $R^3$ is a $C_{15}$ alkyl group.

7. The compound of claim 6 wherein $R^4$ is a $C_{15}$ alkyl group.

8. The compound of claim 5 wherein $R^1$ and $R^2$ are $CH_3$.

9. A composition of matter comprising an effective immunomodulating amount of the compound of claim 1 combined with a pharmaceutically-acceptable liquid vehicle.

10. The composition of claim 9 further comprising a lipopolysaccharide.

11. A liposome comprising a compound of the formula:

(I) [structural formula of compound]

wherein $R^1$ is ($C_1$-$C_9$) alkyl, $R^2$ is ($C_1C_5$) alkyl, and $R^3$ and $R^4$ are individually ($C_6$-$C_{30}$) alkyl groups having about 4–4 double bonds, X is an L-alanine or D-alanine residue; and the pharmaceutically-acceptable salts thereof.

12. The composition of matter wherein the liposome consists essentially of a liposome having a bilayer membrane consisting essentially of 1-palmitoyl-2-oleoyl-phosphatidyl choline and dioleoyl phosphatidyl choline in a weight ratio of about 5:1 to 1:1 and a compound of the formula:

(I) [structural formula of compound]

wherein $R^1$ is ($C_1$-$C_9$) alkyl, $R^2$ is ($C_1$-$C_5$) alkyl, and $R^3$ and $R^4$ are individually ($C_6$-$C_{30}$) alkyl groups having about 0–4 double bonds, X is an L-alanine or D-alanine residue; and the pharmaceutically-acceptable salts thereof.

13. The composition of claim 12 wherien the weight ratio is about 7:3.

14. A method for stimulating the immune response of a mammal comprising administering an effective amount of the composition of claim 1 or 12 in combination with a pharmaceutically acceptable vehicle.

* * * * *

UNITED STATES PATENT AND TRADEMARK OFFICE
CERTIFICATE OF CORRECTION

PATENT NO. : 4,950,645

DATED : August 21, 1990

INVENTOR(S) : Gerald J. Vosika, et al.

Page 1 of 7

It is certified that error appears in the above-identified patent and that said Letters Patent is hereby corrected as shown below:

In the Abstract, at lines 1 and 2, for "dissacharide" read -- disaccharide --.

Column 1, line 20, for "277" read -- 277 --.

At Column 1, line 21, for "Nocardia rubra" read -- Nocardia rubra --.

Column 1, line 26, for "12" read -- 12 --.

At Column 1, line 38, for "15" read -- 15 --.

At column 1, lines 49 and 50, for "N-acetylmuramyl-L-alanyl-D-isoglutamine" read -- N-acetylmuramyl-L-alanyl-D-isoglutamine --.

At Column 1, line 62, for "in vitro" read -- in vitro --.

At Column 1, line 62, for "in vitro" read -- in vivo --.

At Colmun 2, line 61, for "L-enantiomorphs" read -- L-enantiomorphs --.

At Column 2, line 62, for "D-enantiomorphs" read -- D-enantiomorphs --.

At Column 2, line 63, for "DL-mixtures" read -- DL-mixtures --.

At Column 3, line 21, for "L" read -- L --.

At Column 3, line 22, for "D" read -- D --.

UNITED STATES PATENT AND TRADEMARK OFFICE
CERTIFICATE OF CORRECTION

PATENT NO. : 4,950,645

DATED : August 21, 1990

INVENTOR(S) : Gerald J. Vosika, et al.

It is certified that error appears in the above-identified patent and that said Letters Patent is hereby corrected as shown below:

At Column 3, line 24, for "L-alanyl-D" read -- L-alanyl-D --.

At Column 3, line 27, for "L-alanine" read -- L-alanine --.

At Column 3, lines 28 and 29, for "L-alanine-D-isoglutamine-L-alanine (L-Ala-D-isoGln-L-Ala) read --L-alanine-D-isoglutamine-L-alanine (L-Ala-D-isoGln-L-Ala) --.

At Column 3, lines 45-47, for "acetylmuramyl-L-alanine-D-isoglutamine-L-alaninedipalmitoylglycerol (GlcNAcMurNAc-L-Ala-D-isoGln-LDPG" read -- acetylmuramyl-L-alanine-D-isoglutamine-L-alaninedipalmitoylglycerol (GlcNAcMurNAc-L-Ala-D-isoGln-L-DPG --.

At Column 4, line 15, for "18" read -- 18 --.

At Column 4, line 22, for "et seq." read -- et seq. --.

At Column 5, line 12, for "b" read -- by --.

At Column 5, line 45, for "β-D" read -- β-D --.

At Column 5, line 45, for "[D-2" read -- [D-2 --.

At Column 5, line 46, for "L-alanyl-D-isoglutaminyl-L" read -- L-alanyl-D-isoglutaminyl-L --.

At Column 5, line 47, for "D-glucopyranose" read -- D-glucopyranose --.

At Column 5, line 48, for "L-Ala-D-isoGln-L" read -- L-Ala-D-isoGln-L --.

UNITED STATES PATENT AND TRADEMARK OFFICE
CERTIFICATE OF CORRECTION

PATENT NO.  : 4,950,645

DATED       : August 21, 1990

INVENTOR(S) : Gerald J. Vosika, et al.

Page 3 of 7

It is certified that error appears in the above-identified patent and that said Letters Patent is hereby corrected as shown below:

At Column 5, line 56, for "L-alanine" read -- L̲-alanine --.

At Column 5, line 58, for "L-alanine" read --L̲-alanine --.

At Column 6, line 27, for "L-alanine" read -- L̲-alanine --.

At Column 6, line 28, for "L-alanine" read -- L̲-alanine --.

At Column 6, line 28, for "(L-Ala" read -- (L̲-Ala --.

At Column 6, line 41, for "247" read --2̲4̲7̲ --.

At Column 6, line 43, for "241" read -- 2̲4̲1̲ --.

At Column 6, line 65, for "BOC-L-Ala-D" read
-- BOC-L̲-Ala-D̲ --.

At Column 6, line 68, for "L-Ala-D" read -- L̲-Ala-D̲ --.

At Column 7, line 12, for "β-D" read -- β-D̲ --.

At Column 7, line 12, for "[D-2" read -- D̲-2 --.

At Column 7, lines 13 and 14, for "propanoyl-L-alanyl-D-isoglutamine]-D-glucopyranose (GlcNAcMurNAc-L-Ala-D-isoGln)" read -- propanoyl-L̲-alanyl-D̲-isoglutamine]-D̲-glucopyranose (GlcNAcMurNAc-L̲-Ala̲-D̲-isoGln̲) --.

At Column 7, line 16, for "MurNAc-L-Ala-D-isoGln" read
-- MurNAc-L̲-Ala-D̲-isoGln --.

UNITED STATES PATENT AND TRADEMARK OFFICE
CERTIFICATE OF CORRECTION

PATENT NO. : 4,950,645

DATED : August 21, 1990

INVENTOR(S) : Gerald J. Vosika, et al.

It is certified that error appears in the above-identified patent and that said Letters Patent is hereby corrected as shown below:

At Column 7, line 37, for "BOC-L-Ala-DPG" read -- BOC-L-Ala-DPG --.

At Column 7, line 40, for "BOC-L-alanine" read -- BOC-L-alanine --.

At Column 7, line 59, for "BOC-L-Ala-DPG" read -- BOC-L-Ala-DPG --.

At Column 7, line 63, for "L-Ala-DPG" read -- L-Ala-DPG --.

At Column 7, line 65, for "BOC-L-Ala-DPG" read -- BOC-L-Ala-DPG --.

At Column 8, lines 12 and 13, for "Micrococcus lysodeikticus" read --Micrococcus lysodeikticus --.

At Column 8, line 31, for "mq" read -- mg --.

At Column 8, line 53, for "BOC-L-Ala-D-isoGln-OBn" read -- BOC-L-Ala-D-isoGln-OBn --.

At Column 8, line 56, for "BOC-L-alanyl-D" read -- BOC-L-alanyl-D --.

At Column 9, line 3, for "BOC-L-Ala-D read -- BOC-L-Ala-D --.

At Column 9, line 7, for "L-Ala-D-isoGln-OBn" read -- L-Ala-D-isoGln-OBn --.

UNITED STATES PATENT AND TRADEMARK OFFICE
CERTIFICATE OF CORRECTION

PATENT NO. : 4,950,645
DATED : August 21, 1990
INVENTOR(S) : Gerald J. Vosika, et al.

It is certified that error appears in the above-identified patent and that said Letters Patent is hereby corrected as shown below:

At Column 9, line 8, for "BOC-L-Ala-D-isoGln-OBn" read -- BOC-$\underline{L}$-Ala-$\underline{D}$-isoGln-OBn --.

At Column 9, line 17, for "L-Ala-D" read -- $\underline{L}$-Ala-$\underline{D}$ --.

At Column 9, line 21, for "L-Ala-D" read -- $\underline{L}$-Ala-$\underline{D}$ --.

At Column 9, line 32, for "L-Ala-D" read -- $\underline{L}$-Ala-$\underline{D}$ --.

At Column 9, line 45, for "H2O" read -- $H_2O$ --.

At Column 9, line 50, for "H +" read -- $H^+$ --.

At Column 9, line 50, for "H2O" read -- $H_2O$ --.

At Column 9, line 57, for "L-Ala-D" read -- $\underline{L}$-Ala-$\underline{D}$ --.

At Column 9, line 61, for "L-Ala-D" read -- $\underline{L}$-Ala-$\underline{D}$ --.

At Column 10, line 3, for "L-Ala-D" read -- $\underline{L}$-Ala-$\underline{D}$ --.

At Column 10, line 9, for L-Ala-D" read -- $\underline{L}$-Ala-$\underline{D}$ --.

At Column 10, line 10, for "L-Ala" read -- $\underline{L}$-Ala --.

At Column 10, line 11, for "L-Ala-D-isoGln-L" read -- $\underline{L}$-Ala-$\underline{D}$-isoGln-$\underline{L}$ --.

At Column 10, line 17, for "CH2Cl2" read -- $CH_2Cl_2$ --.

At Column 10, line 22, for "L-Ala-DPG" read -- $\underline{L}$-Ala-DPG --.

UNITED STATES PATENT AND TRADEMARK OFFICE
CERTIFICATE OF CORRECTION

PATENT NO. : 4,950,645

DATED : August 21, 1990

INVENTOR(S) : Gerald J. Vosika, et al.

It is certified that error appears in the above-identified patent and that said Letters Patent is hereby corrected as shown below:

At Column 10, line 52, for "BOC-L-Ala-DPG" read -- BOC-$\underline{L}$-Ala-DPG --.

At Column 10, line 56, for "Ethy.1" read -- Ethyl --.

At Column 11, line 4, for "L-Ala-DPG" read --$\underline{L}$-Ala-DPG --.

At Column 11, line 14, for "BOC-L-Ala-isoGln-OBn" read -- BOC-$\underline{L}$-Ala-$\underline{D}$-isoGln-OBn --.

At Column 11, line 14, for "BOC-$\underline{L}$-Ala-D" read -- BOC-$\underline{L}$-Ala-$\underline{D}$ --.

At Column 11, line 36, for "L-Ala-D" read -- $\underline{L}$-Ala-$\underline{D}$ --.

At Column 12, line 1, for "L-Ala-D" read -- $\underline{L}$-Ala-$\underline{D}$ --.

At Column 12, line 37, for "L-Ala-D" read -- $\underline{L}$-Ala-$\underline{D}$ --.

At Column 12, line 51, for "L-Ala-D" read -- $\underline{L}$-Ala-$\underline{D}$ --.

At Column 13, line 22, for "teen" read -- then --.

At Column 13, line 26, for "L-AlaD-isoGln-L" read -- $\underline{L}$-Ala-$\underline{D}$-isoGln-$\underline{L}$ --.

At Column 13, line 31, for "$C_{65}H_{116}N_6O_{221} \cdot 2H_2O$" read -- $C_{65}H_{116}N_6O_{21} \cdot 2\ H_2O$ --.

At Column 15, lines 32 and 33, for "in vitro" read -- $\underline{in\ vitro}$ --.

UNITED STATES PATENT AND TRADEMARK OFFICE
CERTIFICATE OF CORRECTION

PATENT NO. : 4,950,645

DATED : August 21, 1990

INVENTOR(S) : Gerald J. Vosika, et al.

It is certified that error appears in the above-identified patent and that said Letters Patent is hereby corrected as shown below:

At Column 15, line 61, for "LipopolYsaccharide" read -- Lipopolysaccharide --.

At Column 17, line 33, for "$(C_1C_9)$" read -- $(C_1-C_9)$ alyl, --.

At Column 18, line 24, for "4-4" read -- 0-4 --.

Signed and Sealed this

Fourteenth Day of July, 1992

Attest:

DOUGLAS B. COMER

*Attesting Officer*   Acting Commissioner of Patents and Trademarks